| United States Patent [19] | [11] Patent Number: 4,855,508 |
| Chapman et al. | [45] Date of Patent: Aug. 8, 1989 |

[54] ENERGETIC DIETHERS AND PROCESS FOR THEIR PREPARATION

[75] Inventors: Robert D. Chapman, Lancaster, Calif.; John L. Andreshak, Waukegan, Ill.; Scott A. Shackelford, Colorado Springs, Colo.

[73] Assignee: The United States of America as represented by the Secretary of the Air Force, Washington, D.C.

[21] Appl. No.: 93,345

[22] Filed: Sep. 4, 1987

[51] Int. Cl.$^4$ .................. C07C 43/00; C07C 117/00
[52] U.S. Cl. .................................. 568/589; 552/11
[58] Field of Search ....................... 568/589; 260/349

[56]         References Cited
        U.S. PATENT DOCUMENTS

| 3,907,907 | 9/1975 | Frankel et al. | 568/589 |
| 4,341,712 | 7/1982 | Frankel et al. | 568/589 |
| 4,424,398 | 1/1984 | McGuire et al. | 568/589 |

OTHER PUBLICATIONS 82-68113F/32 C8Z-E8113 "Acyclic... Compositions" Frankel et al., 1982.
88 071155/10 "New... Volatility", Koppes et al. 1987.

*Primary Examiner*—Ferris H. Lander
*Attorney, Agent, or Firm*—Jules J. Morris; Donald J. Singer

[57]         ABSTRACT

The invention comprises a novel preparation of energetically substituted diether compounds and novel diether compounds not previously reported. In one embodiment certain isomeric forms of dibromoalkanes are converted to corresponding isomers of bromoalkyl trifluoromethanesulfonate esters by reaction with silver trifluoromethanesulfonate (triflate) in a variety of solvents. The triflate substituent in the bromoalkyl triflate esters is than easily displaced by alcohols, including non-nucleophilic ones such as those that contain nitro. The intermediates are similarly reacted to make energetic diethers, selectively under mild conditons. The energetically substituted diether compounds are particularly useful as energetic curatives and plasticizers for rocket propellant binders as well as stable solid oxidizers and industrial explosives.

16 Claims, No Drawings

ENERGETIC DIETHERS AND PROCESS FOR THEIR PREPARATION

FIELD OF THE INVENTION

This invention relates to a process for preparing a variety of energetic diethers suitable for use as propellant plasticizers and oxidizers.

BACKGROUND OF THE INVENTION

This invention is particularly useful for producing energetically substituted diether compounds, suitable for use as plasticizers and oxidizers in rocket propellants. Plasticization of propellants has been previously achieved by the addition of various other structural types of compounds such as nitroglycerine, butanetriol trinitrate, or formal-type ethers prepared by condensation of an aldehyde with an energetic alcohol.

Some diethers have been synthesized conventionally via trifluoromethanesulfonate (commonly called triflate) ester intermediates made from the corresponding alcohols by a reaction with trifluoromethanesulfonic anhydride. However, this conventional synthesis of triflate esters or ditriflate esters is neither selective nor mild with respect to the reactivity towards certain chemical functional groups which may be present in the alcohol. Specifically, the preferred intermediate triflate substituents can not be selectively placed in the alkane skeleton, and unwanted side reactions may occur. Further, many preferred energetic alcohols cannot be incorporated at all using conventional methods.

More generally, energetic plasticizers, oxidizers, prepolymers, and curatives are preferably of the highest possible energy concentration. Though great strides have been made in improving these energetic compounds, further improvement is desired to allow for the construction of more powerful rocket engines and related devices.

A need therefore exists for a method of preparing energetically substituted diether compounds suitable for use as energetic plasticizers or oxidizers.

A further need exists for improved energetic compounds with increased energy concentrations as compared to conventional propellant compounds.

SUMMARY OF THE INVENTION

The invention comprises energetic diether compounds having the formula R"O—X—OR" wherein R" is an energetic alkyl group, X is an alkane group and O is oxygen. In a preferred embodiment the invention comprises energetic vicinal diether compounds.

An important aspect of the invention is the method of preparing the energetic diether. It comprises the steps of converting a polybromoalkane or polyiodoalkane to a corresponding isomer of triflate or nonaflate by reaction with a metal perfluoroalkanesulfonate salt such as silver triflate in a variety of solvents. The triflate substituent in the iodo- or bromoalkyl triflate ester is easily displaced by alcohols, including non-nucleophilic ones such as those that contain energetic electronegative groups such as nitro. The intermediate product thus formed can be similarly reacted a second time with metal triflate to make energetic alkoxyalkyl triflate esters, which can similarly react with an alcohol, including the same or different energetic alcohol, to make energetic diethers. This process allows selective formation of symmetrically or asymmetrically substituted diethers by substitutions which occur in a stepwise manner under mild reaction conditions.

It is the object of this invention therefore to provide energetic diether compounds for use as plasticizers, oxidizers, and curatives for propellant binders as well as for use as ingredients in industrial explosives such as those used in construction.

A further object of this invention is to provide a new and efficient method for preparing these energetic diether compounds that is both selective and mild.

DETAILED DESCRIPTION OF THE INVENTION

The invention comprises a novel process for the preparation of energetic diethers that permits the synthesis of a variety of energetic diethers including novel, previously unreported, energetic diethers. The invention process utilizes a perfluoroalkanesulfonate such as trifluoromethanesulfonate (abbreviated triflate) or nonafluorobutanesulfonate (nonaflate) esters as intermediates. Preparation of these intermediates utilizes classes of compounds which are available commercial materials, polybromoalkanes or polyiodoalkanes. By proper choice of this reactant (in particular, one with at least one secondary bromine or iodine substituent as well as a second primary or secondary bromine or iodine substituent), the displacement of the bromine or iodine substituents can be effected in a stepwise manner. This displacement is accomplished by reaction with metal triflate or nonaflate salt in a variety of possible solvents, the usual ones being carbon tetrachloride, chloroform, benzene, or nitromethane. In a generalized example we will use dibromoalkane and silver triflate to demonstrate preparation of a diether embodying the principles of this invention. A first substitution with silver triflate occurs preferentially at a more reactive secondary bromine substitutent. The triflate substituent in the intermediate monobromoalkyl triflate ester can be readily displaced by a variety of energetic alcohols, including non-nucleophilic polynitroaliphatic alcohols, as depicted in the reaction scheme below:

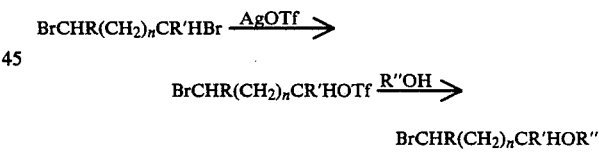

wherein R,R'=alkyl, such as methyl and R"=energetic alkyl, such as 2-fluoro-2,2-dinitroethyl The resulting bromoalkyl energetic alkyl ether (Br—X—OR") can react further, by a scheme similar to that shown above, at the remaining bromine substituent to produce an energetic alkoxyalkyl triflate ester. Likewise, the triflate substitutent in this intermediate can be readily displaced by a variety of alcohols, including energetic non-nucleophilic alcohols in order to form an energetic diether compound (R"O—X—OR").

The invention will be further clarified by a consideration of the working examples below, which are intended to be purely exemplary of the invention.

MATERIALS

Silver trifluoromethanesulfonate (silver triflate) was purchased from PCR/SCM Specialty Chemicals and recrystallized from benzene. The silver triflate-benzene adduct was desolvated by heating (80°–90° C.) overnight in a vacuum oven. Bromoalkanes were purchased commercially and distilled before initial use; solvents were ACS grade. The alcohol, 2-fluoro-2,2-dinitroethanol is not a commercial product, but samples were obtained from the Rocketdyne Division of Rockwell International (Canoga Park, Calif.) and Fluorochem, Inc. (Azusa, Calif.). Other materials used are available commercially.

EXAMPLE I

Preparation of 2,3-Bis(2-fluoro-2,2-dinitroethoxy)butane

The starting material utilized for this example was 2,3-dibromobutane which is an available commercial mixture of 20% dl and 80% meso isomers. Silver triflate (0.450 g, 1.75 mmol) with 3 mL of carbon tetrachloride in a 10-mL flask was initially cooled in an ice-water bath. The 2,3-dibromobutane (0.378 g, 1.75 mmol) in 2 mL of carbon tetrachloride was then added. After stirring at 0° C. for 17 min, 0.121 g potassium carbonate (0.875 mmol) and 0.270 g 2-fluoro-2,2-dinitroethanol (1.75 mmol) were added. The mixture warmed to ambient temperature over the next 3.5 hours, after which it was filtered through a pad of alumina. Chromatography on silica gel-carbon tetrachloride yielded 0.382 g (76% yield) of light yellow liquid, which darkened on standing over a week. This product was distilled at 54°–58° C. (2–3 microns Hg pressure), yielding a clear liquid, identified by $^{13}C$ NMR spectroscopy as the enantiomeric pairs of 2-bromo-3-(2-fluoro-2,2-dinitroethoxy) butane formed from dl- and meso-2,3-dibromobutane.

The bromoalkyl energetic alkyl ether intermediate, 2-bromo-3-(2-fluoro-2,2-dinitroethoxy)butane (0.434 g, 1.5 mmol), in 4 mL carbon tetrachloride was added to 0.385 g (1.5 mmol) of silver triflate in a 10-mL flask. The mixture was warmed to 57° C. in an oil bath. After 47 minutes, 0.234 g (1.5 mmol) of 2-fluro-2,2-dinitroethanol in 2 mL carbon tetrachloride was added. Potassium carbonate, 0.138 g (1.0 mmol), was added after another 45 minutes. Forty-five (45) minutes later, the oil bath heat was turned off and the solution was stirred overnight at ambient temperature. The solution was then filtered through a pad of alumina. Chromatography on silica gel-carbon tetrachloride yielded 0.256 g of light yellow oil, which was a mixture of starting material and product. Medium-pressure liquid chromatography separation, such as on a Michel-Miller system (silica gel-hexane/chloroform) yielded 0.120 g (22% yield) of meso-2,3-bis(2-fluoro-2,2-dinitroethoxy)butane, identified by $^1H$ and $^{13}C$ NMR spectroscopy. This diether is novel in that the ether substituents are positioned on adjacent carbons to form a vicinal diether.

EXAMPLE II

Preparation of 1,4-Bis(2-fluoro-2,2-dinitroethoxy)pentane

The starting material, 1,4 dibromopentane (8.04 g, 35 mmol), was added to a slurry of 9.0 g silver triflate in 50 mL of chloroform at 0° C. in a 100-mL flask with stirring. After one minute, 5.40 g of 2-fluoro-2,2-dinitroethanol (35 mmol) was added. After 5 minutes more, 4.97 g anhydrous sodium sulfate (35 mmol) was added. The mixture was left at 0° C. for 6.5 hours, then was left at ambient temperature overnight. The solution was filtered through a pad of alumina along with 100 mL of chloroform. This solution was washed twice with 100-ml portions of dilute aqueous sodium bisulfite, then twice with 100-mL portions of water. The chloroform layer was then dried over anhydrous sodium sulfate. Chromatography on silica gel-chloroform yielded 6.824 g (64% yield) of light yellow oil which was distilled at 74°–76° C. (3–4 microns Hg pressure) and comprised 1-bromo-4-(2-fluoro-2,2-dinitroethoxy)pentane, as identified by $^1H$ and $^{13}C$ NMR spectroscopy.

The bromoalkyl energetic alkyl ether, 1-bromo-4-(2-fluoro-2,2-dinitroethoxy)pentane (0.758 g, 2.5 mmol), was added to a slurry of 0.642 g silver triflate (2.5 mmol) in 5 mL of carbon tetrachloride at room temperature with stirring in a 10 mL flask. After 30 minutes, 0.385 g of 2-fluoro-2,2-dinitroethanol (2.5 mmol) and 0.173 g of potassium carbonate (1.25 mmol) were added. The flask was fitted with a drying tube containing a desiccant (such as anhydrous calcium sulfate) and left overnight. The solution was then filtered through a pad of alumina. Chromatography on silica gel-carbon tetrachloride yielded 0.434 g (46% yield) of a yellow oil which was an 84:16 mixture of 1,4-bis(2-fluoro-2,2-dinitroethoxypentane with another isomer of bis(2-fluoro 2,2-dinitroethoxy) pentane, according to $^{13}C$ NMR spectroscopy. Separation by medium-pressure liquid chromatography on silica gel-hexane/chloroform yielded pure 1,4-bis(2-fluoro-2,2-dinitroethoxy) pentane in an overall 39% yield from the intermediate 1-bromo-4-(2-fluoro-2,2 dinitroethoxy)pentane.

EXAMPLE III

Preparation of 1,3-Bis(2-fluoro-2,2-dinitroethoxy)butane.

Silver triflate (0.514 g, 2.0 mmol) was dissolved in 5 ml nitromethane in a 10-mL flask, and the solution was cooled to 0° C. in an ice bath. To this was added 0.432 g of 1,3-dibromobutane (2.0 mmol) in 1 mL of nitromethane. After 40 minutes the ice bath was removed; after 1 hour total, 0.308 g fluorodinitroethanol (2.0 mmol) was added, followed in 3 minutes by 0.138 g of potassium carbonate (1.0 mmol). Chromatography on alumina with carbon tetrachloride followed by dichloromethane ($CH_2Cl_2$) yielded 0.344 g (48%) of light yellow oil, 1,3-bis(2-fluoro-2,2-dinitroethoxy)butane, which was identified by $^1H$ and $^{13}C$ NMR spectroscopy.

DISCUSSION OF EXAMPLES

The model alcohol employed in these examples is a very weak nucleophile which demonstrates the useful and unique approach offered by the route utilizing triflate esters as intermediates. The particular route demonstrated with bromoalkane and silver triflate reactants is also unique in offering generally excellent selectivity and mild reaction conditions. In particular, bromoalkane precursors can be used when analogous alcohols are unavailable. Second, certain structural moieties are susceptible to attack by triflic anhydride, which would be used in the alternative conventional alcohol-anhydride route. For example, oxacycloalkane rings (such as epoxides) are generally cleaved by triflic anhydride, whereas epibromohydrin reacts with silver triflate to produce the 2,3-epoxypropyl triflate. Finally, the stepwise selective formations of monobromoalkyl triflates, monoethers derived from them, and ultimately diethers from subsequent displacements are demonstrated here by the syntheses of new ethers of fluorodinitroethanol.

Particularly noteworthy are the syntheses of the first diethers with vicinal fluorodinitroethoxy substituents;

the vicinal incorporation of such electronegative alkoxy substituents has not been reported to be successful by other conventional methods.

A route to vicinally substituted fluorodinitroethyl alkyl ethers was provided by modifying the substrate so that both leaving groups would be secondary, as in Example I where 2,3-dibromobutane was used as a model reactant. In this case, the first metathesis and subsequent nucleophilic substitution occurred facilely at room temperature. Subsequent reaction of 2-bromo-3-(2-fluoro-2,2-dinitroethoxy)butane occurred with silver triflate, then fluorodinitroethanol, in CCl4 (carbon tetrachloride). In most cases, the reaction conditions of the examples were not explored extensively to optimize yields.

The selectivity of the substitution of readily available bromoalkane reactants by even very non-nucleophilic alcohols via triflate intermediates has been proven in the examples by the stepwise syntheses of a variety of mono- and disubstituted alkyl substrates with fluorodinitroethoxy substituents.

The reactivity of primary-secondary and secondary-secondary dibromoalkanes offers on advantage over that of primary-primary dibromoalkanes in that successive steps are generally more distinct, except that the 1,3-dibromoalkanes exhibit unusual behavior in showing nearly equal rates of the successive displacement reactions. 1,3-Dibromopropane could be converted to 3-bromo-1-propyl triflate to the extent of only 66% before 1,3-propanediyl ditriflate formed. Although the reaction of 1,3-dioromobutane (Example III) could be conducted stepwise in carbon tetrachloride, the second step was faster in benzene or in nitromethane, so that the sole product was 1,3-butanediyl ditriflate.

The generality of the transformation of bromoalkanes to alkyl triflates, and subsequent conversion to alkyle thers, is a natural conclusion since its success using the very non-nucleophilic fluorodinitroethanol is now demonstrated. More nucleophilic alcohols, especially those sufficiently economical to use as solvents, would greatly facilitate the reactions involved in this synthetic route.

Equivalents

Other energetic alcohols which would be suitable for energetic diether synthesis by this process are found in the following groups: nitroaliphatic alcohols, nitroolefinic alcohols, nitraminoaliphatic alcohols, azidoaliphatic alcohols, and azidoolefinic alcohols. Some particular examples are 2-nitroethanol; 2,2-dinitroethanol; 2-azido-2,2-dinitroethanol; and 2,2,2-trinitroethanol.

There are also several substrates that may be utilized in this process. In particular the preferred alkane substrates comprise polybromoalkanes and polyiodoalkanes. Some particular dibromoalkane substrates which may be particularly suitable for utilization in this processing include but are not limited to, 1,3-dibromobutane, 2,3-dibromobutane, 1,4-dibromopentane, 1,5-dibromohexane, as well as a variety of specially functionalized dibromoalkane derivatives (such as structures containing additional energetic substituents), providing that the derivatives contain the requisite primary-secondary or secondary-secondary combination of reactive bromine substituents. Thus a variety of energetic diethers can be produced by this stepwise process. In particular, vicinal diethers can now be successfully produced in a stepwise controlled manner. Note that this stepwise process allows for the use of different alcohols in each step, which permits incorporation of different energetic substituents. The examples cited utilized one of the least nucleophilic (and therefore least reactive) of the energetic alcohols which is likely to be of interest for incorporation into propellant formulations (2-fluoro-2,2-dinitroethanol). More nucleophilic alcohols would undergo the described transformation even more readily.

The selectivity of this step-by-step process permits the synthesis of energetic ethers in which the alcohol groups are substituted where desired. The use of different alcohols in the different steps provides the ability to tailor the energy requirement of product. Further, the asymmetry provided by the use of different alcohols during the synthesis can improve the physical properties of the product, particularly pre-polymer products used as propellant binders.

This relatively mild reaction provides a synthesis that is unreactive except in the preferred mode and as a result produces a process that is generally more applicable for producing a desired energetic diether product than conventional syntheses.

This process further permits the synthesis of novel energetic diether products. Vicinal diethers provided by this process will generally be more energetic than conventional diethers in which the energetic groups are separated by largely inert carbons. The production of energetic diethers with fewer unsubstituted carbons produces a higher energy product which may, if desired, have several energetic groups.

INDUSTRIAL APPLICATION

The energetic diethers of this invention can be tailored for a variety of high energy uses including energetic prepolymers, energetic curatives and plasticizers for rocket propellant binders. Stable solid oxidizers can also be produced as well as usably stable explosives for industrial purposes. The high energy nature of the vicinal diethers produced by this process possesses important advantages over conventional materials and may allow production of more powerful rockets and improved spacecraft.

Other embodiments of the invention will be apparent to those skilled in the art from a consideration of this specification or practice of the invention disclosed herein.

Finally, those skilled in the art will recognize or be able to ascertain, using no more than routine experimentation, that there are many equivalents to the specific examples of the invention described herein. Such equivalents are intended to be covered by the following claims.

We claim:

1. An energetic diether having the formula

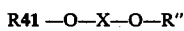

wherein R" is an energetic alkyl moiety selected from the group consisting of 2-fluoro-2,2-dinitroethyl, 2-nitroethyl, 2,2-dinitroethyl, 2-azido-2,2-dinitroethyl and 2,2,2-trinitroethyl, and X is an alkane moiety selected from the group consisting of butyl, pentyl and hexyl.

2. The energetic diether of claim 1 wherein X is butyl.

3. The energetic diether of claim 2 wherein X is 2,3-butyl.

4. The energetic diether of claim 3 wherein R" is 2-fluoro-2,2-dinitroethyl.

5. The energetic diether of claim 2 wherein X is 1,3-butyl.

6. The energetic diether of claim 5 wherein R″ is 2-fluoro-2,2-dinitroethyl.

7. The energetic diether of claim 1 wherein X is pentyl.

8. The energetic diether of claim 7 wherein X is 1,4-pentyl.

9. The energetic diether of claim 8 wherein R″ is 2-fluoro-2,2-dinitroethyl.

10. A method for preparing an energetic diether having the formula

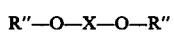
R″—O—X—O—R″ wherein R″ is an energetic alkyl moiety and X is an alkane moiety selected from the group consisting of butyl, pentyl and hexyl which comprises the steps of:

(a) reacting a polyhaloalkane, wherein said halo moiety is bromo or iodo, with a metal perfluoroalkanesulfonate salt to form a haloalkylperfluoroalkanesulfonate first ester;

(b) treating said first ester with an energetic alcohol selected from the group consisting of nitroaliphatic alcohols, halonitroaliphatic alcohols, nitroolefinic alcohols, nitraminoaliphatic alcohols, azidoaliphatic alcohols and azidoolefinic alcohols to form the corresponding haloalkyl energetic ether;

(c) reacting said ether from step (b) with a metal perfluoroalkanesulfonate salt to form a prefluoroalkanesulfonate second ester; and, (d) treating said second ester with said energetic alcohol to form said diether.

11. The method of claim 10 wherein said polyhaloalkane is selected from the group consisting of 1,3-dibromobutane, 1,4-dibromobutane, 2,3-dibromobutane, 2,4-dibromopentane, and 1,5-dibromohexane.

12. The method of claim 10 wherein said energetic alcohol is selected from the group consisting of 2-fluoro-2,2-dinitroethanol, 2-nitroethanol, 2,2-dinitroethanol, 2-azido-2,2-dinitroehtanol and 2,2,2-trinitroethanol.

13. The method of claim 10 wherein said metal perfluoroalkanesulfonate salt is selected from the group consisting of silver triflate, lead triflate, copper triflate, tadmium triflate, silver nonaflate, lead nonaflate, copper nonaflate, mercury nonaflate, and cadmium nonaflate.

14. The method of claim 10 wherein said polyhaloalkane is 2,3-dibromobutane, said metal perfluoroalkanesulfonate salt is silver triflate and said energetic alcohol is 2-fluoro-2,2-dinitroethanol.

15. The method of claim 10 wherein said polyhaloalkane is 1,4-dibromopentane, said metal perfluoroalkanesulfonate salt is silver triflate and said energetic alcohol is 2-fluoro-2,2-dinitroethanol.

16. The method of claim 10 wherein said polyhaloalkane is 1,3-dibromobutane, said metal perfluoroalkanesulfonate salt is silver triflate and said energetic alcohol is 2-fluoro-2,2-dinitroethanol.

* * * * *

UNITED STATES PATENT AND TRADEMARK OFFICE
CERTIFICATE OF CORRECTION

PATENT NO. : 4,855,508
DATED : August 8, 1989
INVENTOR(S) : Robert D. Chapman et al It is certified that error appears in the above-identified patent and that said Letters Patent is hereby corrected as shown below:

In the Abstract, line 9, after "esters is", "than" should read "then".

Col 5, lines 36-37, after "conversion to", "alkyle thers," should read "alkyl ethers,".

Claim 1, line 2, "R41" should read --R"--.

Claim 10, at Col 8, line 2, correct the spelling of "perfluoroalkanesulfonate".

Claim 12, line 4, correct the spelling of "2-azido-2,2-dinitroethanol".

Claim 13, line 4, "tadmium" should read "cadmium".

Signed and Sealed this

Eighth Day of October, 1991

Attest:

HARRY F. MANBECK, JR.

Attesting Officer

Commissioner of Patents and Trademarks